(12) United States Patent
Yvin et al.

(10) Patent No.: US 6,979,665 B2
(45) Date of Patent: Dec. 27, 2005

(54) AGENT FOR STIMULATION OF THE NATURAL DEFENCES OF PLANTS AND METHODS FOR USING IT

(75) Inventors: Jean-Claude Yvin, Saint-Malo (FR); Rozenn Menard, Strasbourg (FR); Serge Kauffmann, Illkirch-Graffenstaden (FR); Bernard Fritig, Souffelweyersheim (FR)

(73) Assignee: Laboratoires Goemar S.A., Saint-Malo Cedex (FR)

( * ) Notice: Subject to any disclaimer, the term of this patent is extended or adjusted under 35 U.S.C. 154(b) by 20 days.

(21) Appl. No.: 10/371,460

(22) Filed: Feb. 20, 2003

(65) Prior Publication Data
US 2004/0110638 A1 Jun. 10, 2004

(30) Foreign Application Priority Data
Feb. 20, 2002 (FR) .......................... 02 02144

(51) Int. Cl.[7] .............................. A01N 43/16
(52) U.S. Cl. .................... 504/117; 504/292; 504/294
(58) Field of Search ................ 504/117, 292, 504/294

(56) References Cited

U.S. PATENT DOCUMENTS

| 5,189,148 A | * | 2/1993 | Akiyama et al. | ........... 530/399 |
| 5,750,472 A | * | 5/1998 | Yvin et al. | .................. 504/292 |
| 6,387,847 B1 | * | 5/2002 | Yvin et al. | .................. 504/117 |

FOREIGN PATENT DOCUMENTS

| FR | 2783523 | 3/2000 |
| WO | WO 94 00993 | 1/1994 |
| WO | WO 99 03346 | 1/1999 |

OTHER PUBLICATIONS

Albersheim et al. APlants Interact with Microbial Polysaccharides@. J. Supramol. Struct. 6(4):599–616. 1977. Boisis Abstrac 78:167923.*

Rouhier et al. AStructural features of fungal β–D–glucans for the efficient inhibition of the initiation of virus infection on Nicotian tabacum@. Phytochemistry. 39(1):57–62. 1995.*

Ozeretskovskaya et al. AOligosaccharins as Regulatory Molecules of Plants@. Russian Journal of Plant Physiology. 43(5):648–655. 1996.*

Mohr et al. Plant Physiology. Springer. P. 558–566. 1995.*

Merck Index, 11th ed. Entry 5226: "Laminaran". p. 844. 1989.*

Alban, S. et al., Synthesis of Laminarin Sulfates with Anticoagulant Activity, Arzneim, Forsch./Drug Res, 1992, pp. 1005–1008, vol. 42, No. 2.

Costet, L. et al., A Pharmacological Approach to Test the Diffusible Signal Activity of Reactive Oxygen Intermediates in Elicitor–Treated Tobacco Leaves, Plant Cell Physiol., 2002, pp. 91–98, vol. 43, No. 1.

Klarzynski, O. et al. Linear β–1,3 Glucans Are Elicitors of Defense Responses in Tobacco, Plant Physiology, Nov. 2000, pp. 1027–1037, vol. 124.

* cited by examiner

*Primary Examiner*—S. Mark Clardy
(74) *Attorney, Agent, or Firm*—McDonnell Boehnen Hulbert & Berghoff LLP

(57) ABSTRACT

The invention relates to a method for the stimulation of the reactions of natural defence of agronomically useful and of decorative plants, characterized by the fact that there is applied on the plants to be treated an aqueous composition comprising an efficient concentration in sulfate of β 1–3 glucan and more particularly a concentration of at least 1 mg/l, preferably of at least 5 mg/l, and still more preferably of at least 10 mg/l in laminarin sulfate, whose degree of sulfatation is higher than or equal to 1.9, preferably from 2 to 2.5, the said composition being applied to the culture or crop to be treated in an amount sufficient to provide per hectare an efficient amount of sulfate of β 1–3 glucan, and in the case of laminarin sulfate in an amount sufficient to provide from 0.4 to 4 g of laminarin sulfate per hectare.

10 Claims, 3 Drawing Sheets

AGENT FOR STIMULATION OF THE NATURAL DEFENCES OF PLANTS AND METHODS FOR USING IT

PRIOR RELATED APPLICATIONS

This application claims priority to French application no. 02 02144, filed Feb. 20, 2002.

The invention relates to an agent for the stimulation of the reactions of natural defences of plants, in particular of plants which are agronomically useful and of decorative plants.

It also relates to the use of the said agent for the stimulation in question and to a method for using it.

The stimulation of the reactions of natural defences of plants is one of the most important present problems and gives rise to very numerous research work.

The said stimulation finds its expression in the case of a plant, which has recognized an attack by a pathogenic agent such as a virus, a bacterium, a fungus or an insect, in the development of a group of biological modifications which put the said plant in condition for resistance enabling the localization of the aggressive agent at the place where it attacks.

Products called elicitors are known which, when put in contact with the plant, are capable to stimulate therein the same reactions of defence as those which are developed by the plant when the latter is attacked by a pathogenic agent.

These reactions of defence correspond to several hereafter recalled types:
- accumulation of natural antibiotics better known under the name of phytoalexins (for example, in the case of tobacco, scopoletin is a phytoalexin, which emits a blue fluorescence under ultra-violet light),
- thickening of the cell walls by synthesis of lignin and of cross-linking proteins,
- synthesis of defence proteins of the kind of the PR proteins (Pathogenesis-Related), which are rearranged in different families among which certain have chitinase activities (family PR3) or glucanase activities (family PR2) or furthermore enzymes of the secondary metabolic pathways such as orthodiphenol-0-methyltransferases or OMT, which are involved in the synthesis of the phytoalexins and in the thickening of the walls,
- synthesis of secondary messengers such as salicylic acid, which is involved, especially in the case of tobacco, in the stimulation of the acidic isoforms of the PR proteins and ethylene, which is involved especially in the case of tobacco, in the stimulation of the basical or alcaline isoforms of the PR proteins.

Among the above said elicitors, it is possible to make mention of the oligo β 1–3 glucans and especially of laminarin, who elicit in the case of various agronomically useful plants the defence reactions in question; the maximum responses are generally reached when the oligo β 1–3 glucans are used in the form of liquid compositions whose concentration in oligo β 1–3 glucans is of the order, i.e. of about 200 mg/l; these responses remain at a comparable level until a concentration of about 4 g/l; they are obtained when the amounts used per hectare are from 4 to 200 g.

In view of the always increasing demand by the user of products which are more and more efficient, the applicant company has continued its research works and has found that in the case of the oligo β 1–3 glucans and especially of laminarin, which is a particular glucan whose degree of polymerisation is from 20 to 30, preferably from 23 to 25, it becomes possible, in an entirely surprising and unexpected manner, to essentially increase the faculty of stimulation of the natural defence reactions of plants when subjecting the latter to a chemical sulfatation reaction which, in the case of laminarin, is conducted in order to bring the degree of sulfatation to a value equal or higher than 1.9, preferably from 2 to 2.5.

Consequently, the sulfates of β 1–3 glucans and especially the sulfate of laminarin can be used as elicitors in the form of aqueous compositions, whose concentration in sulfated derivative is surprisingly and unexpectedly to a considerable extent lower than the concentration in unsulfated β 1–3 glucans, especially in unsulfated laminarin of the compositions of the prior art; furthermore, the amount of β 1–3 glucan sulfate and especially of laminarin sulfate, which must be used per hectare is also in a considerable extent lower than the amount of unsulfated β 1–3 glucans and especially laminarin, which are necessary to obtain the requested stimulation.

Consequently, the agent according to the invention for the stimulation of the reactions of natural defence of the here-above identified plants is consisting of a β 1–3 glucan sulfate and especially of laminarin sulfate whose degree of sulfatation is higher than or equal to 1.9, preferably from 2 to 2.5.

The invention relates to the use of the sulfates of β 1–3 glucans and especially of laminarin as agents for the stimulation of the reactions of natural defences of plants.

It also relates to a method for the stimulation of the reactions of natural defence of plants, characterized by the fact that there is applied on the plants to be treated an aqueous composition comprising an efficient concentration in sulfate of β 1–3 glucan and more particularly a concentration of at least 1 mg/l, preferably of at least 5 mg/l, and still more preferably of at least 10 mg/l in laminarin sulfate, whose degree of sulfatation is higher than or equal to 1.9, preferably from 2 to 2.5, the said composition being applied to on the culture or crop to be treated in an amount sufficient to provide per hectare an efficient amount of sulfate of β 1–3 glucan, and in the case of laminarin sulfate in an amount sufficient to provide from 0.4 to 4 g of laminarin sulfate per hectare.

The higher limit of the concentration in β 1–3 glucan sulfate of the compositions used according to the invention is not a critical feature; in practice and in the case of laminarin sulfate, a concentration higher than 500 mg/l does not provide any better result.

The research work on the results of which is based the here-above defined invention results from the following statements.

As far as, above all, the active substance proper is concerned, i.e. the sulfate of laminarin, it can be obtained along the hereafter disclosed manner, being known that the other β 1–3 glucans are obtained by methods disclosed in the scientific literature.

Laminarin, which is marketed by the applicant company under the trade mark PHYCARINE can be extracted starting from a raw material consisting of brown algae, especially using the method disclosed in the French patent FR 92 08387.

Figure 1:
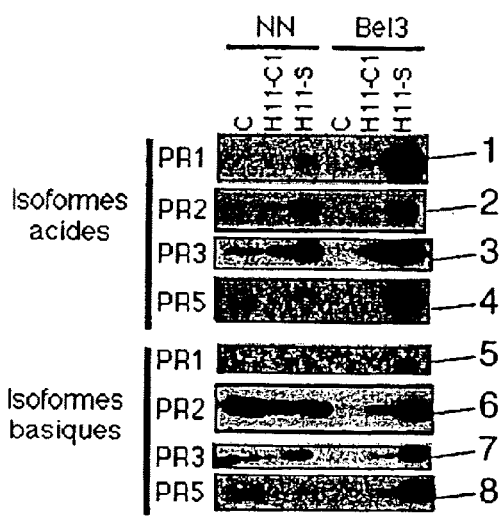
FIG. 1 shows the results of immunodetection analysis of proteins.

The sulfatation of that laminarin can be carried out by way of the method disclosed in the following publication:

Alban S, Kraus J, Franz G: Synthesis of laminarin sulfates with anticoagulant activity, Arzneim. Forsch./drug Res (1992) 42; 1005–1008.

An improved method of sulfatation of laminarin is disclosed in the thesis of Susanne Alban, presented in 1993 at the University of Regensburg under the title "Synthese und physiologische Testung neuartiger Heparinoide".

These methods enable to obtain a laminarin sulfate, which is highly substituted without degradation and with a good reproducibility under good conditions from the economical stand point of view, while remaining simple.

These methods can be adapted to the sulfatation of β 1–3 glucans in general.

In order to obtain an efficient sulfatation of laminarin without degradation or decomposition of the polysaccharidic chains, the reaction of sulfatation must be carried out under conditions, which correspond to an absolute absence of water.

Before the sulfatation, the laminarin is dried, for example on phosphor pentoxide ($P_2O_3$) and then dissolved in dimethyformamide or DMF. Due to its alternative effects on the polysaccharide, DMF presents in activating influence on the substitution. As a matter of fact, the association of polar DMF with the OH groups leads to the cleavage of the intra and inter molecular hydrogen links and to the disintegration of the superior structures.

In order to carry out the sulfatation reaction, it is possible to use advantageously the complex $SO_3$-pyridin.

As a result of the coordination of the acceptor of electrons $SO_3$ with the donor of electrons pyridin, the reactivity of $SO_3$, which is difficult to be controlled and which gives rise to highly exothermic reactions leading to degradations, is reduced. The complex $SO_3$-pyridin presents with respect to other complexes the advantage of being neither too reactive nor too stable, i.e. too slow from the point of view of the reaction.

Due to the fact that the degree of sulfatation obtained is proportional to the molecular excess in sulfatation reagent and due to the fact that the aim is to obtain a degree of substitution higher than 2, a concentration of 6 moles of $SO_3$-pyridin per mole of glucose is advantageously used.

In order to warrant the absence of water it is possible to work under argon atmosphere.

Furthermore, from the beginning of the reaction, pyridin is added to the reagent of sulfatation in equimolar amount in order to directly catch the sulphuric acid, which could be formed by reaction of the complex $SO_3$-pyridin with water. The concentration of the laminarin as well as the concentration of the reagent of sulfatation must be as high as possible due to the fact that the solubility of the polysaccharide and of the sulfatation reagent are limiting. In order to avoid at the beginning of the reaction a cooling of the mixture, which might rise to problems of solubility and in order to obtain a substitution as regular as possible, the solution of the complex $SO_3$-pyridin within DMF might be added not in one time but continuously during 4 hours.

The reaction of sulfatation can be carried out at a temperature from 20 to 60° C., preferably of about 40° C. Higher temperatures would lead to a more efficient substitution but also to a degradation of the chains.

After the addition of the reagent of sulfatation, the mixture is further stirred during 6 hours at 60° C. At that temperature, a supplemental substitution occurs without degradation of the chains.

The supernatant of the mixture is separated by decantation. The residual matter is dissolved in an amount of 2.5 M of NaOH, and then mixed with 10 times its volume of ethanol of 90%. The precipitate, which forms at a temperature from 4–8° C. during the night is separated and then dissolved in diluted sodium hydroxide (solution having a pH of about 9). The solution is dialysed in order to remove the salts and the molecules of low molecular weight using a membrane of the type Spectrapor having a separation threshold of 1000 D and then brought to a pH of 7.0 by addition of NaOH and then lyophilised. The resultant sulfate of laminarin is in the form a sodium salt.

The molecular weight of the macromolecule is determined as hydrodynamic volume by chromatography on gel using a system called "Fast Protein Liquid Chromatography" or FPLC, marketed by the company Pharmacia. The detection of the elution profile (eluant: 0.1 M NaCl with 0.05% sodium azide, 30 ml/h) using a device known under the trademark Superdex 75HR10/30 (domain of separation 3–70 kd) is carried out by the measurement of the refraction index. The laminarin sulfate corresponds to a symmetric narrow peak; the width of said peak is the same in the case of unsulfated laminarin as in the case of sulfated laminarin, which suggests that the length of the chains remains the same. The relative molecular weight is determined using a standard curve with pullulans (standard polymer: 5800-85300 d, Polymer Laboratories, Separation Science Division). Due to the presence of the sulphate groups, which are highly hydrated, the hydrodynamic volume is higher than the actual molecular mass.

The degree of sulfatation is determined by conductimetric titration of the free acid of the sulfated polysaccharide using sodium hydroxide 0.1 N or by way of ionic chromatography after hydrolysis using a HPLC system. The first method presents the advantage of being also adapted to investigations concerning the stability (the consumption of sodium hydroxide increases when the sulfate groups are eliminated) while the HPLC method needs less substance and can be automatized. For sake of control, it is possible to determine the content in sulfur by elementary analysis.

It is furthermore possible to control the homogeneity of the sulfatation and the distribution of the sulfate groups on the different positions in the glucose molecule by way of a modified form of the analysis of methylation followed by an GC-MS examination (i.e. Chromatography Gas, Masse Spectrometry). The sulfatation if practically total, which means that almost all of the hydroxyl groups in position 6 are sulfated. At the moment of the substitution of the secondary OH groups, there is no longer any significative difference between the sulfatation of the groups in position 2 and the one of the groups in position 4.

The degree of sulfatation obtained proceeding as hereabove indicated is higher than 1.9 and more precisely from 2 to 2.5.

The degree of polymerisation of the laminarin sulfate thus obtained is from 20 to 30, and more precisely from 23 to 25.

Within the frame of the above said works, the stimulation of the reaction of the natural defences obtained in agronomically useful plants and in decorative plants has been examined especially in the case of tobacco, the treatment of the said plants having been carried out on the one hand by using non sulfated laminarin (code H11) and on the other hand by using sulfated laminarin (code H11-S).

Three batches of unsulfated laminarin, respectively designated by H11-C1, H11-C2 and H11-C3 have been used; the second and the third batch are those, which were used for the further chemical sulfatation and constitute consequently the actual "control" with respect to the sulfated laminarin.

The treatment has been applied on the one hand to the whole plants and on the other hand to cellular suspensions, the varieties of the plants used being:

the variety *Nicotiana tabacum* cv. Samsun NN designated by NN the variety *Nicotiana tabacum* cv. Bel3 designated by Bel3

The cellular suspensions here above mentioned are suspensions obtained starting from the vegetal tissue of *Nicotiana tabacum* cv. Bright Yellow.

First, the plants of the varieties NN and Bel 3 as such were treated using aqueous compositions comprising respectively the fractions H11-C1 and H11-S at the concentration of 200 mg/l, which is, as indicated hereabove, the optimum dosis for the elicitor activity of unsulfated glucans.

The treatment consists in the infiltration of the above said aqueous compositions based on the fractions H11-C1 and H11-S into the mesophyl of the leaves of the treated plants.

The infiltration is carried out by piercing tobacco leaves using a needle and by applying then perpendicularly with respect to the plane of the leave a syringe containing the solution to be injected. Immediately after the injection, the infiltration zone, visible by illumination of the leave from its lower face, is delimited using a felt type pen. The infiltrated zone is designated by ZI.

From the symptomatological stand point of view, it is noticed that the tissues infiltrated with H11-C1 do not present any sign of alteration while those infiltrated with H11-S present a depigmentation.

That depigmentation appears through a loss of the green colour at the level of the infiltrated tissues.

Furthermore and still at the level of the tissues infiltrated with H11-S a blue fluorescence under U.V. light is observed.

That fluorescence is due to the accumulation of scopoletin.

In a first time, the influence of the composition based on H11-C1 and on H11-S on the induction of typical defence responses such as the expressions of the PR proteins and the OMT activity has been studied.

Concerning the PR proteins, the expression of the acidic and of the alkaline isoforms of 4 families of these proteins, i.e. the families PR1, PR2, PR3 and PR5 has been analysed in the case of tobacco plants of the varieties NN and Bel3 infiltrated with compositions based on the fractions H11-C1 and H11-S at a concentration of 200 mg/l. It is noticed that it is more important in the zones infiltrated by H11-S than in the zones infiltrated by H11-C1.

The analysis of these proteins has been carried out by immunodetection as disclosed in the publication in the name of Costet L., Dorey S., Fritig B. and Kauffmann S., published under the title:

"*A pharmacological approach to test the diffusible signal activity of reactive oxygen intermediates in elicitor-treated tobacco leaves*", in Plant Cell and Physiology (2002) 43; 91–98.

The results obtained by this analysis are collected in FIG. 1.

That FIG. 1 shows on the tracks 1 to 8 the induction of the acidic proteins PR1, PR2, PR3 and PR5 as well as those of the alkaline proteins PR1, PR2, PR3 and PR5 in the case of the varieties NN and Bel3 infiltrated on the one hand with water (symbol C) as control, on the other hand with the composition having a concentration of 200 mg/l of H11-C1 and the other hand again with the composition having a concentration of 200 mg/l of H11-S.

The intensity of the induction appears on the tracks 1 to 8 by way of spots more or less pronounced.

The examination of these spots on the tracks of FIG. 1 shows that the effect is clearly more pronounced in the case of variety Bel3 and stronger in the case of the composition based on H11-S.

Measurement was also made of the OMT activity induced by the compositions based on the fractions H11-C1 and H11-S.

For the measurement of that activity, procedure was as disclosed by Costet L., Dorey S., Fritig B. and Kauffmann S in the publication here above identified and published under the title:

"*A pharmacological approach to test the diffusible signal activity of reactive oxygen intermediates in treated-treated tobacco leaves*", in Plant Cell and Physiology (2002) 43; 91–98.

Figure 2:
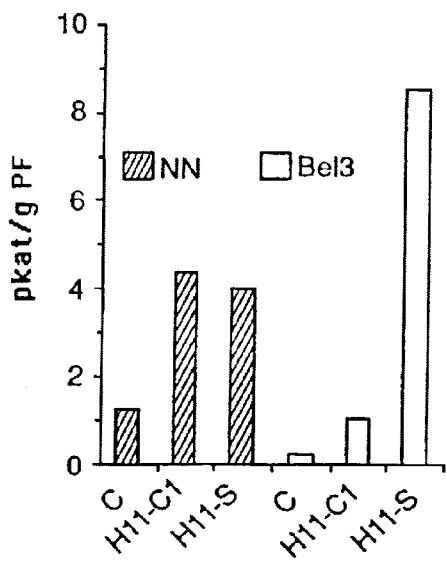
FIG. 2 shows measurement of OMT activity induced by the compositions based on the fractions H11-C1 and H11-S.

The results as obtained are illustrated by FIG. 2.

The latter show the stimulation of the OMT activity, expressed in pkat/g FP (i.e. in picokatal per gram of fresh product FP, in other words of fresh vegetable material), by infiltration with water as control (reference C), then with the compositions based on H11-C1 and H11-S, the plants treated being again the varieties NN and Bel3.

The stimulation is clearly more intense with the composition based on H11-S in the case of the variety Bel3.

On the contrary, it is similar for the compositions based on H11-C1 and on H11-S in the case of the variety NN.

Starting from the results shown on FIG. 2 with respect to the variety Bel3, it is possible to forecast that in order to obtain a stimulation of the OMT activity equal to that obtained with a composition based on H11-C1 at a concentration of 200 mg/l it would be sufficient to use a composition based on H11-S of a concentration of about 8 to 9 times lower.

The same experience of expression of the acidic proteins was carried out looking more particularly for the expression of the acidic PR1 protein in the varieties NN and Bel3 treated on the one hand with water as control (C) and in the other hand with five aqueous compositions respectively based on the fractions H11-C1, H11-C2, H11-C3, H11-S and H16 all of which had a concentration of 200 mg/l, the fraction H16 being based on polyfucanes, which are naturally sulfated polysaccharides.

Figure 3:
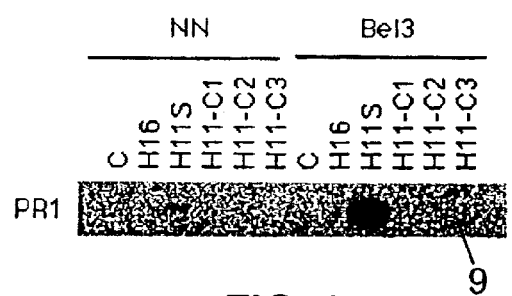
FIG. 3 shows that the highest expression is obtained with H11-S.

The samples of infiltrated tissues on which the treatments illustrated by track 9 of FIG. 3 were made, were carried out 3 days after the infiltration treatment.

The intensity of the spots that appear on track 9 shows that the highest expression is obtained with H11-S, especially in the case of the variety Bel3.

The OMT activity has also been measured after infiltration of the varieties NN and Bel3 with the same compositions.

Figure 4:
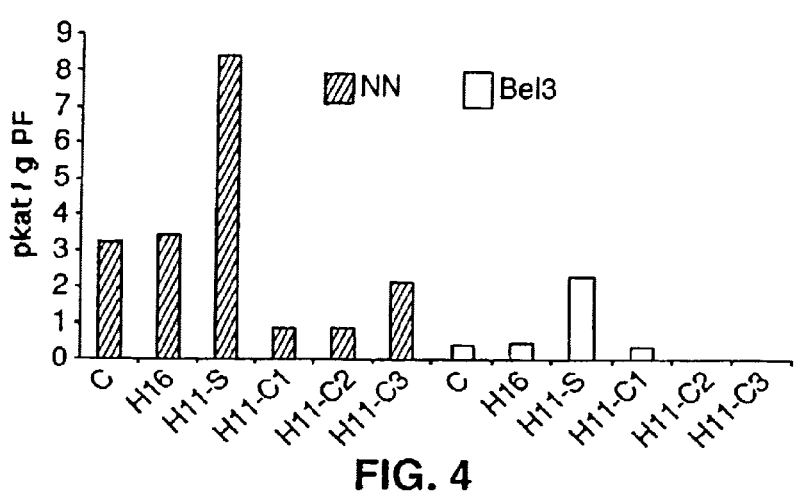
FIG. 4 shows that the results obtained with H11-S are better than those obtained with H16 and with the control fractions.

The results obtained are shown on FIG. 4, which shows the thus obtained stimulation of the OMT activity expressed in pkat/g FP.

When examining FIG. 4, it is noticed that the results obtained with H11-S are clearly better than those obtained with H16 and with the control fractions C, H11-C1, H11-C2, H11-C3.

These results authorize to come to the same conclusions as those drawn from FIG. 2, i.e. that a composition based on H11-S and whose concentration is eight times lower than a composition based on the fractions H11-C1, H11-C2 and H11-C3 permits to obtain a comparable result.

Furthermore, as well in the case of the expression of the acidic PR1 protein (FIG. 3) than in the case of the stimulation of the OMT activity (FIG. 4) the low activity noticed for the compositions based on H16, i.e. based on naturally sulfated polyfucanes, shows that the improvement of the stimulation obtained when using sulfated laminarin with respect to unsulfated laminarin was unexpected and surprising.

The stimulation, after infiltration with the here above defined compositions H11-C and H11-S of the accumulation of salicylic acid and of scopoletin in the varieties NN and Bel3 was then examined.

Figure 5:
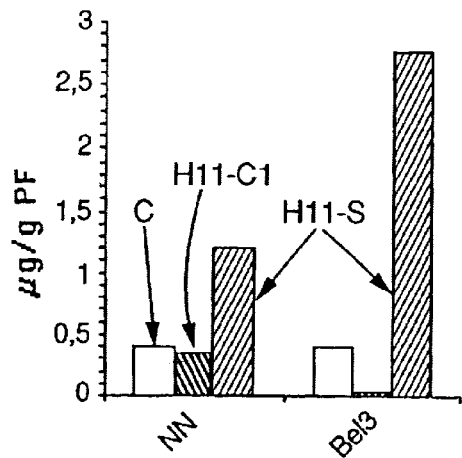
FIGS. 5 and 6 show the accumulation of total salicylic acid and of the total scopoletin determined on infiltrated tissues.
Figure 6:
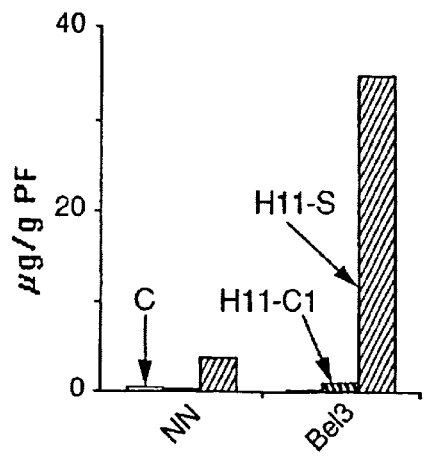

The results of these experiences appear on FIGS. 5 and 6, which respectively show the accumulation—expressed in $\mu$g respectively of salicylic acid and of scopoletin per gram of infiltrated tissues—of the total salicylic acid (free and conjugated forms) and of the total scopoletin (free and conjugated forms) determined on tissues on the varieties NN and Bel3 infiltrated as indicated here above on the one hand with water (C) as a control and on the other hand with compositions based on the fractions H11-C1 and H11-S containing respectively 200 mg/l of these fractions, the infiltrated tissues being sampled 3 days after the infiltration treatment.

Here again, it clearly appears that as well for the accumulation of salicylic acid as for that of scopoletin a given result obtained with a composition having a concentration of 200 mg/l of fraction H11-C1, can be obtained with a composition based on fraction H11-S essentially lower, the ratio of the concentrations, which is the most important in the case of the variety Bel3 being able to reach the number 30.

From the totality of these experiences, it appears that the chemical sulfatation increases in a very important manner the elicitor activity of the responses of the natural defences of the treated plants.

That increase in scopoletin is all the more unexpected and surprising as it does take place in the case of the other sulfated oligoglucanes, here the fucanes, only with an intensity much lesser, of the order of 5 to 10 times as far as scopoletin in concerned and of the order of 2 to 5 times lesser as far as the salicylic acid is concerned.

These facts permit to contemplate treatments with aqueous compositions, whose concentrations in active substance, here in sulfate of $\beta$ 1–3 glucans and especially in laminarin sulfate and the amounts used per hectare in active substance are much lesser, especially in proportions according to those indicated, than the concentrations and amounts per hectare necessary in the case of unsulfated $\beta$ 1–3 glucans and especially of unsulfated laminarin.

In another line of tests or experiences, the varieties NN and Bel3 have been treated with inducing compositions presenting respectively the concentrations of 0.5 and then of 5, of 20, of 50, of 200 and of 1,000 mg/l in H11-S and H11-C2 and the expression of the PR1 and PR2 acidic proteins in the case of the said varieties NN and Bel3 have been analysed.

The said tests or experiences show that the more the concentration in sulfated laminarin is high, the more the symptoms of chlorosis are severe.

Furthermore, the first symptoms of fluorescence under UV light are obtained at doses of 50 mg/l of sulfated laminarin.

Figure 7:
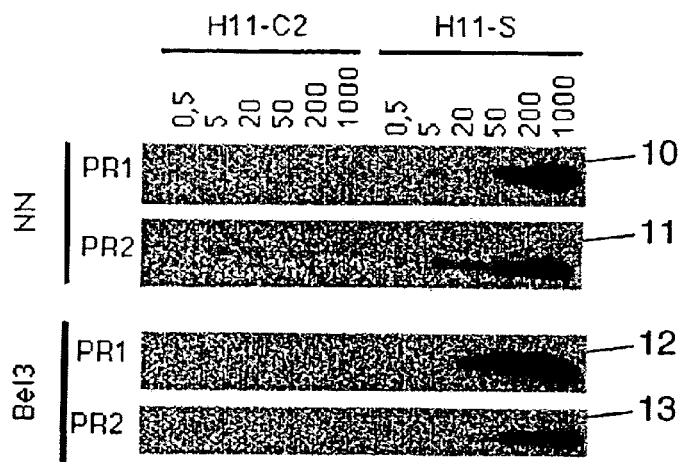
FIG. 7 shows the influence of the concentration of the composition used on the expressions of the acidic PR1 and PR2 proteins, which has been determined by immunodetection.

FIG. 7 shows the influence of the concentration of the composition used on the expressions of the acidic PR1 and PR2 proteins, which has been determined by immunodetection.

That expression of the acidic PR1 and PR2 proteins is materialised by the intensity of the spots, which appear on the tracks 10, 11, 12, 13, and which are the result of the determination by immunodetection.

More especially, it results from FIG. 7 that the acidic PR1 and PR2 proteins are detected as soon as concentrations of from 5 to 20 mg/l are used as far as H11-S is concerned, while these same proteins are hardly detectable even at concentrations of 1,000 mg/l of unsulfated laminarin H11-C2.

In another line of tests, the varieties NN and Bel3 have been treated with the same inducing compositions presenting respectively the concentrations of 0.5 and then of 5, of 50, of 200 and of 500 mg/l in H11-S and H11-C and the OMT activity in the case of the varieties NN and Bel3 has been analysed.

Figures 8, 9:
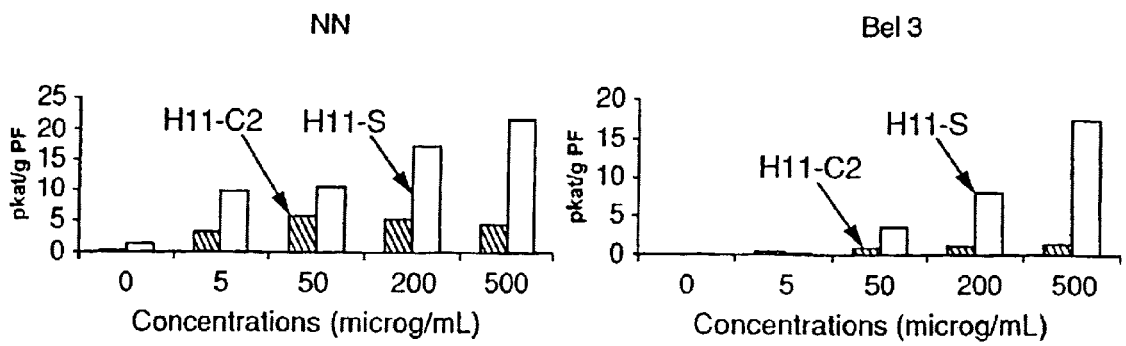
FIGS. 8 and 9 show the values of stimulation of the OMT activity respectively in the case of the varieties NN and Bel3.

FIGS. 8 and 9 show the values of stimulation of the OMT activity (expressed in pkat/g FP) respectively in the case of the varieties NN and Bel3.

It appears from these figures that the OMT activity increases progressively as a function of the concentrations in H11-S and H11-C2, but much faster in the case of H11-S.

In a general manner, the maximum response as far as the expression of the PR proteins and of the OMT activity is concerned is reached at a dosis of 500 mg/l of sulfated laminarin, concentration at which the OMT activity is in the case of the variety NN about four times and in the case of the variety Bel3 about ten times higher than that obtained after treatment of the same varieties with H11-C2.

Complementary experiences have shown that the treatments with H11-S induce the signalisation pathways of salicic acid and of ethylene, which control the stimulation of a whole set of defence responses. From a practical point of view, these facts suggest that the treatments with H11-S also induce defence with responses different from those here described.

Other experiences have been carried out on cellular suspensions along the here above indications.

One of these experiences is consisting of the so-called alkalinisation test of the extracellular medium and the other of the so-called test of the refractory state.

In the case of the first test, the latter is carried out on a cellular suspension obtained starting from vegetable tissues of the variety Bright Yellow. To three 8 ml samples of that cellular suspension were added respectively 160 $\mu$l of three aqueous compositions respectively containing 10 g/l of the fractions H11-C1, I25 (oligofucanes) and H11-S, the final concentration in each of the oligosaccharides being equal to 200 mg/ml.

The addition of the compositions based on H11-C1 or on I25 induces after 10 minutes a strong alkalinisation of the medium (1.5 pH units) while the addition of the composition based on H11-S induces at the end of the same duration a very low alkanilisation (0.3 pH units).

That result is surprising due to the fact that the man skilled in the art normally should have expected according to the results of the preceding comparative experimentations carried out on unsulfated glucans and on sulfated fucans a correlation between the intensity of the alkanilisation response of the medium and the intensity of the induction of the defence responses; however, the contrary has been noticed on the one hand as far as unsulfated laminarin and the sulfated oligofucans are concerned and on the other hand as far as sulfated laminarin is concerned, this being a further argument in favour of the fact that the invention implies the inventive activity necessary to be patentable.

As far as the test of the refractory state is concerned, it consists to proceed as indicated in the publication of Karzinsky O., Plesse B., Joubert J. M., Yvin J. C., Kopp M., Kloareg B., and Fritig B. in "Plant Physiology (2001) 124; 1027–1037 under the title "*Linear β-1,3 glucans are potent elicitors of defence responses in tobacco*".

Within the frame of this test, first a 8 ml volume of cellular suspension has been treated by a volume of 160 μl of an aqueous composition containing 10 g/l of the fraction H11-S (final concentration in H11-S of 200 μg/ml). As soon as the pH is returned to the starting value, after transitory alkanilisation of the medium such as here above described, 160 μl of an aqueous composition containing 10 g/l of the fraction H11-C1 (final concentration in H11-C1 of 200 μg/ml) have been added.

Parallely, the same volume of cellular suspension has been treated successively with the same volumes as above indicated of aqueous compositions containing respectively 10 g/l of fractions H11-S and I25.

The variation of the pH in function of the time expressed in minutes has been measured during 160 minutes, which provides the curves C1 (FIG. 10) and C'1 (FIG. 11) respectively for the first and the second experiences.

Then the same experiences are carried out again, the difference being the reversal of the succession of the treatments; in another words, in the first case the cellular suspension is first treated by the composition based on H11-C1 and then by the composition based on H11-S and in the second case the composition based on I25 is first introduced and then the composition based on H11-S.

The same pH measurements were made and curves C2 (FIG. 10) and C'2 (FIG. 11) were obtained.

Figure 10:
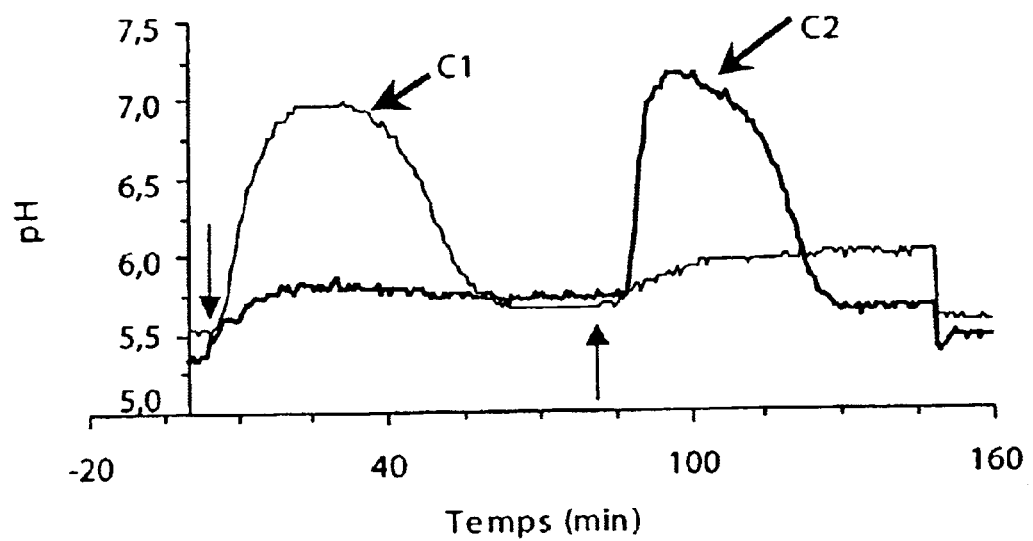
FIGS. 10 and 11 show the variation of pH as a function of time with compositions based on H11-S/H11-C1 and H11-S/I25, respectively.
Figure 11:
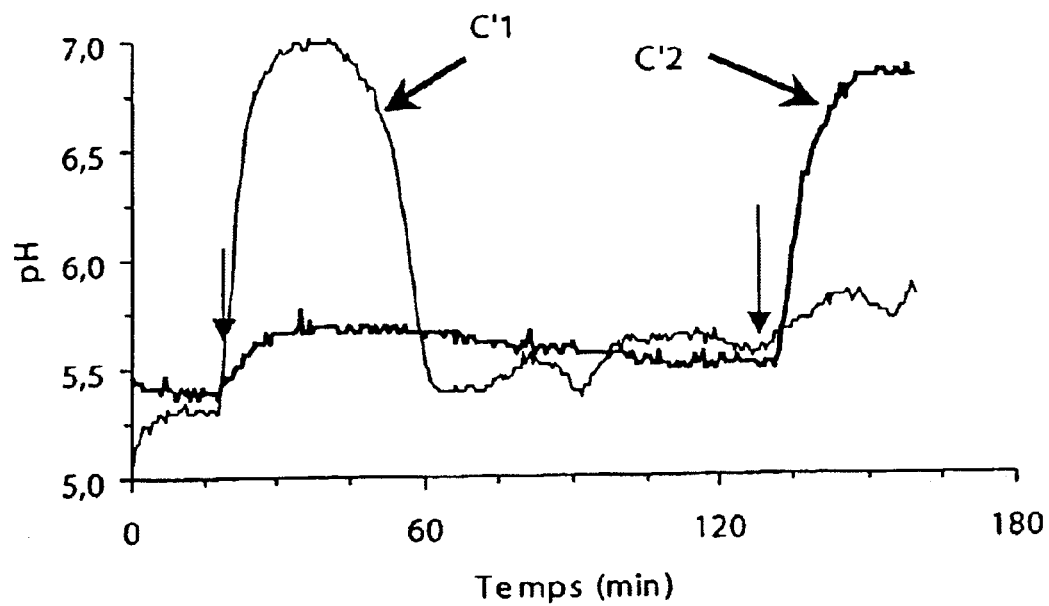

When examining FIGS. 10 and 11, it appears that the response to the first treatment has no interaction with the alkalinisation response of the medium after the second treatment (curves C1 and C'1).

The reversal or inversion of the treatments (curves C2 and C'2) confirms that absence of refractory state, this word meaning that the cells, which specifically discern a molecule X, react alcanalising the medium and that they are no longer capable to perform that reaction if the same molecule is added a few minutes later the said cells being at that time still capable to perform the said reaction if a molecule Y, discerned in a different manner than the molecule X, is added.

By way of consequence, the sulfated β 1–3 glucans and especially sulfated laminarin might be discerned specifically as they are not recognized by the same receptor as the receptor of the unsulfated β 1–3 glucans and especially the unsulfated laminarin and of the sulfated fucans.

From a practical stand point of view, it follows that the chemical sulfatation of the β 1–3 glucans and especially of laminarin provides new molecules, which are probably discerned differently than the unsulfated β 1–3 glucans and especially unsulfated laminarin and that the combination of these 2 types of molecules respectively unsulfated and sulfated might have a synergistic effect in connection with the activation of the defence responses of the plants.

What is claimed is:

1. A method for stimulation of natural defensive reactions of agronomically useful plants and of decorative plants, comprising applying to the plant to be treated, an aqueous composition comprising an efficient concentration of sulfated β 1–3 glucan wherein the sulfated β 1–3 glucan comprises a degree of sulfatation equal to at least 1.9.

2. The method of claim 1, wherein the aqueous composition comprises a concentration of at least 1 mg/L of sulfated β 1–3 glucan, and wherein the sulfated β 1–3 glucan comprises a degree of sulfatation from 2 to 2.5.

3. The method of claim 1, wherein the aqueous composition comprises a concentration of at least 5 mg/L of sulfated β 1–3 glucan, and wherein the sulfated β 1–3 glucan comprises a degree of sulfatation from 2 to 2.5.

4. The method of claim 1, wherein the aqueous composition comprises a concentration of at least 10 mg/L of sulfated β 1–3 glucan, and wherein the sulfated β 1–3 glucan comprises a degree of sulfatation from 2 to 2.5.

5. A method for stimulation of natural defensive reactions of agronomically useful plants and of decorative plants, comprising applying to the plant to be treated, an aqueous composition comprising an efficient concentration of laminarin sulfate, wherein the laminarin sulfate comprises a degree of sulfatation equal to at least 1.9.

6. The method of claim 5, wherein the aqueous composition comprises a concentration of at least 1 mg/L laminarin sulfate, and wherein the laminarin sulfate comprises a degree of sulfatation from 2 to 2.5.

7. The method of claim 5, wherein the aqueous composition comprises a concentration of at least 5 mg/L laminarin sulfate, and wherein the laminarin sulfate comprises a degree of sulfatation from 2 to 2.5.

8. The method of claim 5, wherein the aqueous composition comprises a concentration of at least 10 mg/L laminarin sulfate, and wherein the laminarin sulfate comprises a degree of sulfatation from 2 to 2.5.

9. The method of claim 1, wherein the aqueous composition is applied in an efficient concentration per hectare to stimulate the natural defensive reactions of agronomically useful plants and of decorative plants.

10. The method of claim 5, wherein the aqueous composition is applied in an concentration of 0.4 to 4 g of laminarin sulphate per hectare.

* * * * *